United States Patent [19]
Zhou et al.

[11] Patent Number: 5,308,771
[45] Date of Patent: May 3, 1994

[54] CHEMICAL SENSORS

[75] Inventors: Quan Zhou, Newton Centre; Mary E. Tabacco, Brighton; Bruce N. Nelson, South Boston, all of Mass.

[73] Assignee: Geo-Centers, Inc., Newton Centre, Mass.

[21] Appl. No.: 868,028

[22] Filed: Apr. 13, 1992

[51] Int. Cl.$^5$ ............................................. G01N 21/00
[52] U.S. Cl. .................... 436/39; 422/82.06; 422/82.07; 422/82.08; 422/82.11; 427/2; 436/41; 436/111; 436/113; 436/134; 436/142; 436/166; 436/172
[58] Field of Search .......... 422/82.06–82.08, 422/82.11; 436/111–113, 41, 39, 134, 172, 166, 527, 533, 534, 142; 427/2

[56] References Cited

U.S. PATENT DOCUMENTS

| | | | |
|---|---|---|---|
| Re. 31,879 | 5/1985 | Lubbers et al. | 436/133 |
| 4,059,685 | 11/1977 | Johnson | 436/527 X |
| 4,321,057 | 3/1982 | Buckles | |
| 4,399,099 | 8/1983 | Buckles | 422/58 |
| 4,557,900 | 12/1985 | Heitzmann | 422/55 |
| 4,560,248 | 12/1985 | Cramp et al. | |
| 4,800,886 | 1/1989 | Nestor | 128/634 |
| 4,861,727 | 8/1989 | Hauenstein et al. | 436/136 |
| 5,124,130 | 6/1992 | Costello et al. | 422/82.06 |

OTHER PUBLICATIONS

Seitz, W. R., "Chemical Sensors Based on Fiber Optics", Analytical Chemistry, vol. 56, No. 1, Jan. 1984.
Peterson, J. I., Fitzgerald, R. V., "Fiber-Optic Probe for in Vivo Measurement of Oxygen Partial Pressure", Analytical Chemistry, vol. 56, No. 1:62–67, Jan. 1984.
Shahriari, M. R., Zhou, A. and Sigel, Jr., G. H., "Porous optical fibers for high-sensitivity ammonia-vapor sensors," Optics Letters, vol. 13, No. 5:407–409, May 1988.
Zhou, A., Shahriari, M. R., Kritz, D., and Sigel, Jr., G. H., "Porous Fiber-Optic Sensor for High-Sensitivity Humidity Measurements," Analytical Chemistry, vol. 60, No. 20:2317–2320, Oct. 15, 1988.
Zhou, Q. and Sigel, Jr., G. H., "Porous polymer optical fiber for carbon monoxide detection," SPIE vol. 1172, Biochemical And Environmental Sensors, pp. 157–161, (1989).
Zhou, Q. and Sigel, Jr., G. H., "Detection of carbon monoxide with a porous polymer optical fibre," International Journal of Optical Electronics, vol. 4, No. 5,:415–423 (1989).
Tabacco, M. B. and Zhou, A., "Chemical Sensors for CELSS Application," 21st International Conference on Environmental Systems, San Francisco, Calif., SAE Technical Paper Series 911360, Jul. 18, 1991.
Tabacco, M. B., Rosenblum, K., Zhou, Q., Shariari, M. R., "Chemical Sensors for Environmental Monitoring," 93rd Annual Meeting, The American Ceramic Society, Cincinnati, Ohio, Solid State Optical Materials Symposium, Dec. 30, 1991.
Zhou, A., Kritz, D., Bonnell, L., and Sigel, Jr., G. H., "Porous plastic optical fiber sensor for ammonia measurement," Applied Optics, vol. 28, No. 11:2022–2025, Jun. 1, 1989.
Zhou, A., Tabacco, M. B., Rosenblum, K., "Development of Chemical Sensors Using Plastic Optical Fiber," No. 1592-13 presented at SPIE, O/E Fibers, Boston, Mass., Sep. 1991.
Tabacco, M. B., Zhou, A., and Nelson, B., "Chemical Sensors for Environmental Fiber Sensors III," vol. 1587 presented at SPIE, Boston, Mass. Sep. 4–5, 1991.

Primary Examiner—Jill A. Johnston
Attorney, Agent, or Firm—Wolf, Greenfield & Sacks

[57] ABSTRACT

A device for detecting the presence or concentration of an analyte, a method of making the device, and a method of detecting the presence or concentration of an analyte. The invention features one or more supports, such as beads, which carry a thin film of polymer substrate. The polymer substrate has a sensing reagent and a porous matrix. The sensing reagent alters the optical properties of the polymer substrate in the presence of analyte.

51 Claims, 4 Drawing Sheets

CHEMICAL SENSORS

FIELD OF THE INVENTION

The present invention features reliable, reversible, inexpensive, portable and miniaturizationable devices for measuring the concentration of chemicals in a fluid media. Embodiments of the present invention have application in the detection of toxic gases, for monitoring water quality and for monitoring on line equipment and processes. The sensors feature porous polymers in which selective sensing reagents have been immobilized. The porous polymers are immobilized on supports.

BACKGROUND OF THE INVENTION

Optical sensors for detection of chemicals have been described by several individuals. One type of optical sensor (sometimes referred to as an optrode) is characterized by a porous polymer capable of receiving and interacting with the selected analyte.

Porous polymer sensors offer excellent interaction with analyte along the optical path length. The porous polymer sensors chemically bind the sensor reagent to the polymer to prevent the sensing reagent from washing out, particularly in aqueous phases.

The porous polymer sensors react with the analyte of interest resulting in a change in the optical properties of the polymer. The porous polymer sensors can be used for in situ detection of atmospheric trace contaminants and dissolved gases and chemicals.

However, porous polymer sensors require a diffusion time to equivocate to the concentration of the media in which they are surrounded. Embodiments of the present invention feature a porous polymer sensor having an improved reaction time.

SUMMARY OF THE INVENTION

The present invention features a device for detecting the presence or concentration of an analyte, a method of making the device, and a method of detecting the presence or concentration of an analyte. One embodiment of the device for detecting the presence or concentration of an analyte comprises support means enclosed or encased in a polymer substrate. The polymer substrate is capable of receiving and discharging light. The polymer substrate has a porous matrix and a sensing reagent. The sensing reagent has a first absorption spectra in the presence of analyte and a second absorption spectra in the absence of analyte. The porous matrix expands the surface area of the polymer substrate, for receiving analyte in the presence of sensing reagents. The support means is a material capable of providing mechanical strength to the polymer substrate. The porous matrix held on the support means allows the sensing reagent, to interact with analyte, to alter the spectra of light passing through polymeric substrate. The light passing through the polymeric substrate is monitored for such changes in spectra which changes are indicative of the presence or concentration of analyte.

The term "analyte" is used in a broad context to refer to any molecule or groups of molecules for which information as to the presence or concentration is desired.

Devices made in accordance with the present invention are suitable to detect the presence or concentrations of any analyte capable of directly or indirectly interacting with a sensing reagent held in the porous matrix of the polymer substrate. Typical examples of analytes include, without limitation, hydrogen ion, hydrazine, ethylene, carbon monoxide, ammonia and water.

Preferably, the sensing reagent is substantially dispersed within the polymer substrate. The sensing reagent is bonded to or entrapped by the polymer substrate and thus immobilized. Typical examples of sensing reagents are, without limitation, bromophenol red, bromocresol purple, vanillin, cobalt chloride and palladious chloride.

The device of the present invention can be selective to numerous analytes due to the selection of the sensing reagent and the ability to alter the conditions of forming the porous matrix to provide a selective porous matrix.

The term "porous matrix" is used in the present application to suggest a volume with surface texture, indentations, grooves and openings, which expands the total effective surface area of the polymer substrate beyond the surface area of the support. In the context of the porous matrix, pores or openings do not necessarily suggest complete discrete passages with well defined entrances or exits. Electron microscopic examination of preferred porous matrices of the present invention reveal a pore, opening, or spanning of grooves of approximately 50 angstroms and 200 angstroms. The polymer substrate forms a thin film on the surface of the bead. The thin film may have a thickness of up to 200 microns.

The device of the present invention can also be made selective by a selection of the polymeric substrate. Hydrophilic substrates such as 2-hydroxyethyl methacrylate and polyacrylamide will readily receive hydrophilic analytes.

The polymeric substrate can be hydrophobic with substrates comprised of methacrylate and triethylene glycol dimethacrylate. Hydrophobic substrates are suitable for detecting gaseous molecules in liquid or other gaseous molecules.

The hydrophilic polymeric substrate can be readily expanded by polymerizations in the presence of water to form a porous matrix. Hydrophobic polymeric substrates are readily expanded by a polymerization process in the presence of an organic solvent during the polymeric reaction. The inorganic or organic solvents are removed to create the porous matrix. A preferred organic solvent is octane.

Coating support means with the polymer substrate provides an additional enhancement of the interaction area of the media containing analyte and the areas of the porous matrix having a sensing reagent.

A preferred support means is a glass bead. Preferably, support means comprise a plurality of beads having a diameter of approximately 100 to 1000 microns, and, most preferably, 400 microns. However, any support which can be readily handled and provides consistency in shape and performance may be used. The support provides mechanical support for the polymer substrate. The porous matrix is carried on the support as a thin film, minimizing diffusion distances for analyte. The term "substantially enclosed or encased" means the support means has a covering, which covering extends over a large part of the support, but not necessarily all. One embodiment of the present invention features a plurality of beads, in which irregularities in the covering, thickness and features of each bead tend to be less significant when considered as a group.

Preferably, the device comprises light inputting and discharging means. Such light inputting and discharging means are used to direct light from a light source into the polymer substrate and for receiving light leaving the polymer substrate. A preferred light inputting and discharging means features a housing which holds the polymer substrate in communication with one or more optical fibers.

One housing features a cylindrical wall defining an interior chamber, an exterior surface and two ends. One of the ends has an optical fiber for directing light into the interior chamber and one of the ends has an optical fiber for receiving light from the interior chamber. The interior chamber is in communication with the exterior surfaces by openings in the cylindrical wall. The support means enclosed within a polymer substrate is contained within the interior chamber.

Embodiments of the present device feature the benefits of both the porous glass and porous polymer chemical sensors. The sensing reagent is chemically bonded to or entrapped by the polymer substrate providing stability in aqueous phases. The composition of the starting materials allows the matrix to be altered in favor of the analyte over other molecules likely to be present, allowing the analyte to preferentially interact with the sensing reagent.

The device of the present invention features a short response time. The beads carry the porous polymer substrate as a thin film. The analyte may diffuse quickly through the thin film polymer, assuming the concentration that the analyte has in the media. Diffusion distances are smaller than devices which feature larger polymer matrix volumes.

A further embodiment of the present invention features a method of detecting the presence or concentration of an analyte. The method comprises the steps of contacting a sample potentially containing analyte with at least one support means substantially enclosed in a polymer substrate. The polymer substrate is capable of receiving and discharging light. The polymer substrate has a porous matrix and sensing reagent. The sensing reagent has a first absorption spectra in the presence of analyte and a second absorption spectra in the absence of analyte. The porous matrix expands the surface area of the polymer substrate for receiving analyte in the presence of sensing reagent. Support means comprise a material capable of providing mechanical strength to the polymer substrate. The polymer substrate receives and discharges light at the first and second absorption spectra allowing the sensing reagent to alter the spectra of light passing through the polymeric substrate in the presence or absence of analyte. The method further comprises the step of monitoring the polymer substrate for a change in the absorption spectra indicating the presence or absence of analyte.

A still further embodiment of the present invention features a method of making a device for detecting the presence or concentration of an analyte. The method comprises the steps of forming a support means substantially enclosed in a polymer substrate. The polymer substrate has a porous matrix and a sensing reagent. The sensing reagent has a first absorption spectra in the presence of analyte and a second absorption spectra in the absence of analyte. The support means comprises a material capable of providing mechanical strength to the polymer substrate. The porous matrix is capable of receiving analyte in the presence of sensing reagent. The polymeric substrate is capable of receiving and dispersing light at the first and second absorption spectra allowing the sensing reagent to alter the spectra of light passing through the polymeric substance in the presence or absence of analyte.

Preferably, the support means substantially enclosed in a polymer substrate is made by combining the support means with monomers capable of forming the polymer substrate in the presence of the sensing reagent and solvents. The monomers are polymerized and after the polymerization reaction is completed, the solvent is removed. The solid support encased in or enclosed in the polymer substrate. The sensing reagent is substantially dispersed within the polymer substrate. The removal of the organic solvent creates a porous matrix within the polymer substrate.

The present invention can be used with supporting instrumentation. Preferably, the supporting instrumentation comprises light emitting diodes for inputting light into the polymer substrate. A preferred light emitting diode comprises a green light emitting diode which acts as an active interrogation wave length and a red light emitting diode which acts as an optical reference. A light emitting diode driver circuit regulates the output intensity of the light emitting diodes. A modulation circuit independently modulates the light emitting diodes. A detector circuit demodulates the signal and provides a lock in amplifier function. The signal from the detector circuit undergoes an analog to distal conversion for signal processing and display as required. Signal conditioning for on line calibration is performed in software.

The use of two wave-lengths in the supporting instrumentation allows for correction for various mechanical, optical and environmental effects during the measurement of the light received from the polymer substrate.

The active optical signal overlaps the absorption band of the sensing reagent. The second wave length serves as a reference signal, having spectral separation from the measurement wave length. The ratio of the active to reference intensities compensates for variations in the connector, fiber bending and detector response. The ratio also provides substantial immunity to other sensor related interferences, such as refractive index change of the solution, biofouling and sensory mechanical defects and indicator loss.

Preferably, the dual wave length optical sources, detectors, data acquisition and signal conditioning electronics are integrated on a standard PC bus board with outputs and inputs adapted to be received by a PC type computer capable of handling the data through appropriate software.

The software for the optrode system performs several functions. It includes routines to test the functionality of the interface boards and generate error messages should problems be detected. It generates commands to control the operation of the interface board such as turning on and off light emitting diodes, controlling gain, and acquiring data from the analog to digital converter. These commands are sequenced to read data from the sensor as well as compensate for ambient light conditions and changes in luminosity by the optical sources. The signal processing routines incorporate all these data to generate a normalized ratiometric output that is calibrated by a polynomial curve fit to pH or other chemical parameter or species. Routines to allow on line calibration are provided so that calibrations may be updated or generated for different sensors.

BRIEF DESCRIPTION OF THE DRAWINGS

The invention will be described with reference to the drawings, which describe, by way of illustration, preferred embodiments of the invention, and should not be construed as limitations of the invention described in the claims.

DETAILED DESCRIPTION OF THE INVENTION

Embodiments of the present invention will be described in detail as chemical sensors for the detection or concentration determination of analytes. The analytes selected for detailed discussion are hydrazine, carbon monoxide, ammonia and hydrogen ion. Individuals skilled in the art will readily recognize that embodiments of the present invention can be modified to detect the presence of concentration of any analyte. The detailed description which follows is intended to exemplify features of the present invention and should not be construed as limiting the invention in any manner.

Figure 1:
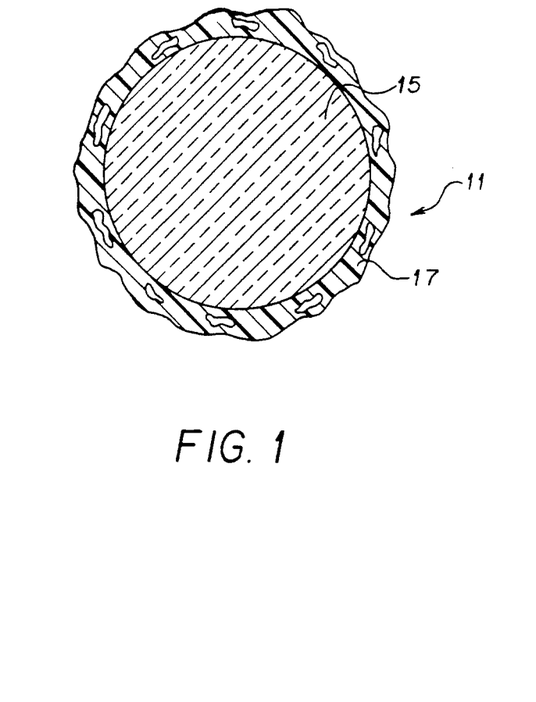
FIG. 1 illustrates in cross sectional view a support enclosed or encased in a polymer substrate embodying features of the present invention.

Turning now to FIG. 1, a device for detecting the presence or concentration of an analyte is generally designated by the numeral 11. The device is comprised of the following major elements, support means in the form of a glass bead 15 and a polymer substrate 17. Polymer substrate 17 is capable of receiving and discharging light. The polymer substrate is illustrated in FIG. 1 as having a porous matrix.

Dispersed within the polymer substrate is sensing reagent (not shown). The sensing reagent has a first absorption spectra in the presence of analyte and a second absorption spectra in the absence of analyte. The sensing reagent is bonded to or entrapped by the polymer substrate.

The bead 15 provides mechanical strength to the polymer substrate 17 as a porous matrix. The polymer substrate 17 receives analyte in the porous matrix. The sensing reagent alters the spectra of light passing through the polymeric substrate 17 in the presence or absence of analyte.

The light leaving polymer substrate 17 is monitored for such changes in spectra indicative of the presence or concentration of analyte.

The polymer substrate is prepared by a copolymerization technique. An admixture is made of monomers, an inert and soluble component solvent, a sensing reagent and beads, and a polymerization reaction is started with chemical initiators or radiation. After polymerization, the inert solvent is removed from the polymer to leave an interconnecting porous structure around the bead supports. The monomers may be hydrophilic or hydrophobic. One example of hydrophilic monomers is 2-hydroxyethyl methacrylate and polyacrylamide. One example of a hydrophobic monomer is methylmethacrylate and triethylene glycol dimethacrylate.

Any organic and inorganic liquids can be used as an inert solvent. Preferred solvents comprise octane and water.

The physical properties of the cross linked polymer network can be altered for a specific application. The factors which influence the physical properties of the cross-linked polymer network include the solvent properties, amount and type of solvent and the quantity of cross-linking agent employed. Smaller quantities of cross-linker may cause the polymer substrate to have nonpermanent porosity. A large quantity of cross-linker may impart brittleness to the polymer substrate.

A insufficient amount of inert solvent creates a polymer substrate with inadequate porosity. A large quantity of inert solvent gives rise to excessive numbers of pores and may cause a polymer substrate to become opague.

A preferred support means comprises glass beads having a diameter of approximately 400 μm. However, other materials of various sizes and shapes may also be used. Beads are preferred because of the uniformity of the shape and size which promotes formation of a more uniform thin film on the support. The thin film typically is less than 200 microns in thickness.

Figure 2:
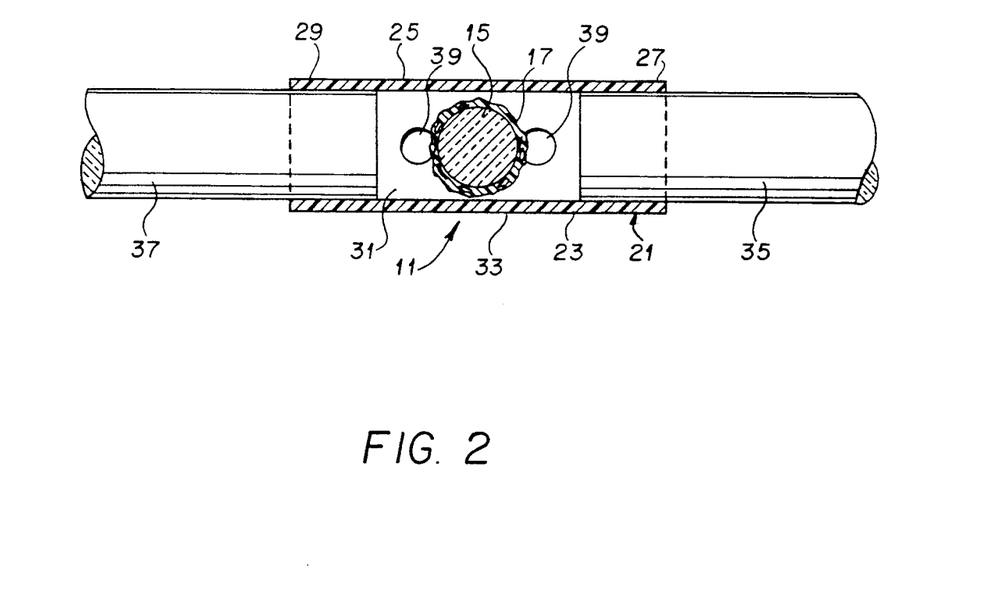
FIG. 2 illustrates in cross sectional view a support enclosed or encased in a polymer substrate held in a light inputting and discharging assembly embodying features of the present invention.

Turning now to FIG. 2, the device 11 for detecting the presence or concentration of an analyte is illustrated further comprising a light inputting and discharging assembly designated by the numeral 21. The assembly is comprised of the following major elements; a housing 23 having a cylindrical wall 25 and two ends 27 and 29. The cylindrical wall 25 and ends 27 and 29 define an interior chamber 31 and an exterior surface 33.

One of the ends, 27, has an optical fiber 35 for directing light into the interior chamber 31. The other end, 29, has an optical fiber 37 for receiving light from the interior chamber 31.

For the purpose of the illustration, the interior chamber 31 contains only one bead 15 enclosed in a polymer substrate 17. Normally, the chamber 31 would contain a plurality of beads 15 enclosed in a polymer substrate 17.

The interior chamber 31 is in communication with the exterior surface 33 by means of openings 39 in the cylindrical wall 25. The openings 39 in cylindrical wall 25 allow fluid media to circulate within the interior chamber 31 and become in contact with the polymer substrate 17.

Light directed into the interior chamber 31 through optical fiber 35 is received by the polymer substrate 17 on bead 15 and, in the presence of analyte, is altered. The light is passed by the polymer substrate 17 through the interior chamber 31 to optical fiber 37.

Figure 3:
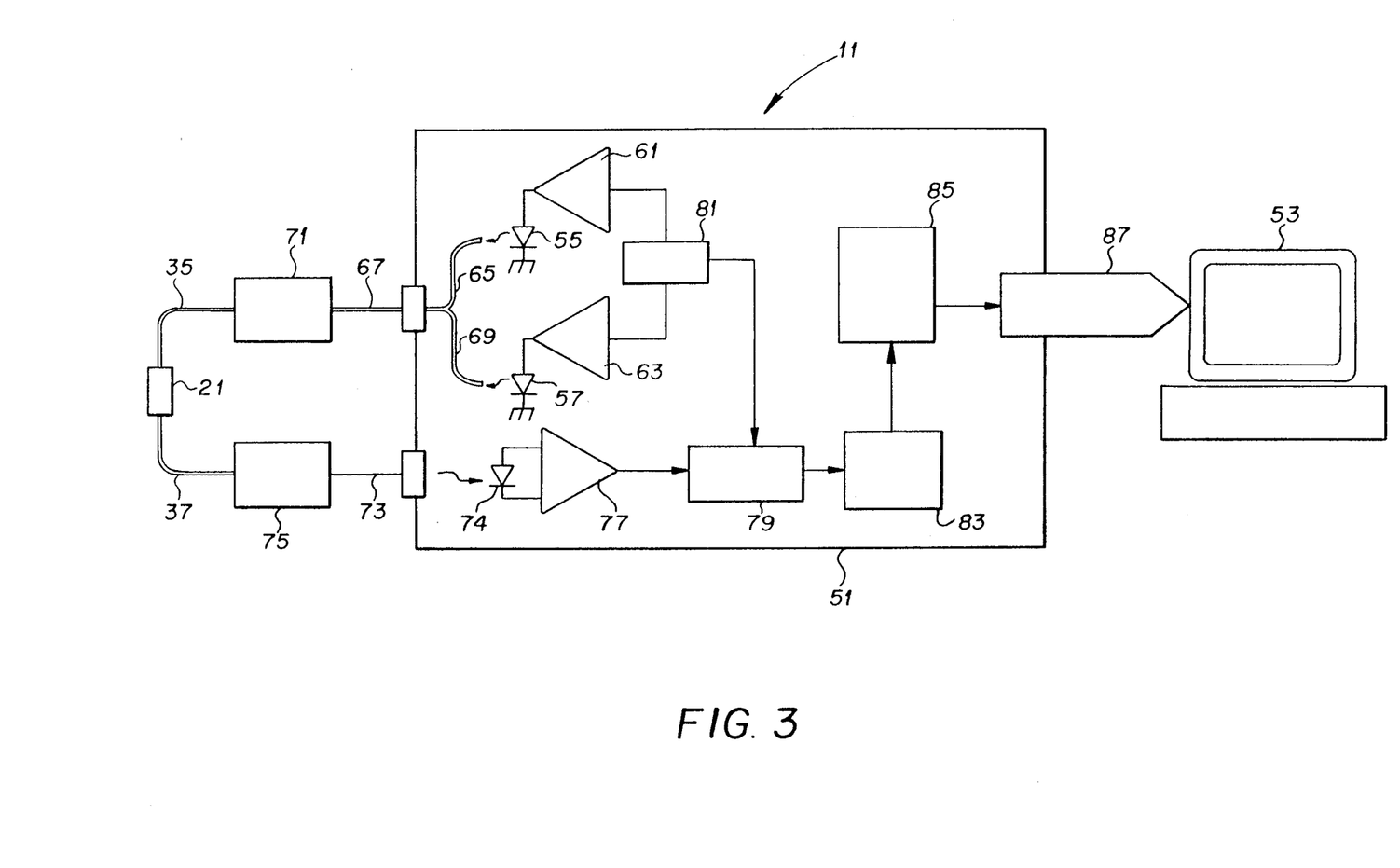
FIG. 3 illustrates in block diagram form a light inputting and discharging assembly with an electronic support assembly embodying featured in the present invention.

Turning now to FIG. 3, the device for detecting the presence or concentration of an analyte is again generally designated by the numeral 11. The device is comprised of the following further elements: a light inputting and discharging assembly designated generally by the numeral 21, containing a bead 15 enclosed within a polymer substrate 17 as described with respect to FIGS. 1 and 2, a board assembly 51, and a computer 53. The board assembly 51 and computer 53 allow the processing of the information from the light inputting and discharging assembly 21.

The board assembly 51 features two light emitting diodes 55 and 57. Light emitting diode 55 is powered by a light emitting diode driver 61 and light emitting diode 57 is powered by light emitting diode driver 63.

The light emitting diode 55 produces a reference signal which is received by fiber coupler 65 in communication with an optical fiber 67.

Light emitting diode 57 produces a signal light which is received by fiber coupler 69 in communication with optical fiber 67.

Optical fiber 37 of the inputting and discharging assembly 21 is connected to the optical fiber 67 through a connector 71.

Light received by optical fiber 35 is inputted into the interior chamber 31 of the light inputting and discharging assembly to be received by a polymer substrate 17 held as thin film on a bead 15 as shown in FIGS. 1 and 2. Light leaving the interior chamber 31 is received by optical fiber 37. Optical fiber 37 is connected to a detection optical fiber 73 by connector 75. The signal is received by a diode 74 in a detector amplifier assembly 77 and passed to a demodulator 79.

The demodulator 79 also receives signals from a modulator 81 in communication with the light emitting diode drivers 61 and 63. The signal from the demodulator is received by a timing control 83 and an AD converter 85. AD converter 85 sends signals through bus interface and device registers 87 to computer 53. Computer 53 processes the signals to produce information with respect to the presence or concentration of analyte.

Other features of the present invention will be apparent from the following specific examples.

EXAMPLE 1

Example 1 is directed to embodiments of the invention for measuring hydrogen ion concentration. Acrylamide (11.6 weight percent), N,N-Methylene bisacrylamide (0.95 weight percent), 2,2'-Azobis 2-amidino propane (0.58 weight percent), distilled water (86.6 weight percent), and bromophenol red (0.28 weight percent) were combined with glass beads. Each bead had an approximate diameter of 400 microns.

The monomers were polymerized in the presence of the glass beads forming a porous matrix of the polymer substrate on each bead. The polymerization reaction was initiated and completed in a low temperature oven. After polymerization, the glass beads are washed to remove any remaining solvent.

The spectral absorption pattern of the sensing agent, bromophenol red, bonded or entrapped in the polymer substrate, is different in the presence of hydrogen ion.

EXAMPLE 2

Example 2 is directed to embodiments of the invention for measuring ammonia concentration. Methyl methacrylate (54.0 weight percent), triethylene glyol dimethacrylate (32.0 weight percent), octane (13.72 weight percent), and bromocresol purple (0.28 weight percent) were combined with glass beads. Each bead had an approximate diameter of 400 microns. Polymerization inhibition in methyl methacrylate was eliminated by alkali water rinsing and removal of the water with magnesium sulfate.

The monomers were polymerized in the presence of the glass beads forming a porous matrix of the polymer substrate on each bead. The polymerization reaction was initiated with benzoyl peroxide and completed in a low temperature oven. After polymerization, the glass beads are washed in acetone to remove any remaining solvent.

The spectral absorption pattern of the sensing agent, bromocresol purple, bonded or entrapped in the polymer substrate, is different in the presence of ammonia.

EXAMPLE 3

Example 3 is directed to embodiments of the invention for measuring hydrazine ion concentration. Methyl methacrylate, triethylene glycol dimethacrylate, octane, and vanillin are combined with glass beads. Each bead has an approximate diameter of 400 microns.

The monomers are combined in a concentration effective for polymerization in the presence of the solvent octane, and the sensing agent vanillin. Generally, methyl methacrylate will have a concentration of approximately 50-60 weight percent, triethylene glycol dimethacrylate will have a concentration of approximately 25-35 weight percent, and octane will be present in a concentration of approximately 5-15 weight percent.

The sensing agent vanillin will be present in a concentration which allows for losses in the postpolymerization rinses. Generally, the sensing agent will have a concentration of approximately 0.1-1.0 weight percent.

The monomers are polymerized in the presence of the glass beads forming a porous matrix of the polymer substrate on each bead. The polymerization reaction is initiated with benzoyl peroxide and completed in a low temperature oven. After polymerization, the glass beads are washed to remove any remaining solvent.

The spectral absorption pattern of the sensing agent, vanillin, bonded or entrapped in the polymer substrate, is different in the presence of hydrazine.

EXAMPLE 4

Example 4 is directed to embodiments of the invention for detecting ethylene or carbon monoxide. Methyl methacrylate, triethylene glycol dimethacrylate, octane, and palladious chloride were combined with glass beads. Each bead had an approximate diameter of 400 microns.

The monomers are combined in a concentration effective for polymerization in the presence of the solvent octane, and the sensing agent palladious chloride. Generally, methyl methacrylate will have a concentration of approximately 50-60 weight percent, triethylene glycol dimethacrylate will have a concentration of approximately 25-35 weight percent, and octane will be present in a concentration of approximately 5-15 weight percent.

The sensing agent palladious chloride will be present in a concentration which allows for losses in the postpolymerization rinses. Generally, the sensing agent will have a concentration of approximately 0.1-1.0 weight percent.

The monomers are polymerized in the presence of the glass beads forming a porous matrix of the polymer substrate on each bead. The polymerization reaction is initiated and completed with benzoyl peroxide in a low temperature oven. After polymerization, the glass beads are washed in acetone to remove any remaining solvent.

The spectral absorption pattern of the sensing agent, palladious chloride, bonded or entrapped in the polymer substrate, is different in the presence of ethylene or carbon monoxide.

EXAMPLE 5

Example 5 is directed to an assembly for inputting and discharging light signals from the beads. The beads, encased in a polymer substrate, were packed into a tube of 1000 to 1500 microns in internal diameter. The site of the tube is primarily a matter of convenience based upon the size of the beads encased in the polymer substrate. The larger the bead the larger the tube.

The porous tube was approximately 1 to 3 cm long and made of stainless steel or plastic. A preferred plastic tube is marketed under the trademark Delrin ®. The tube was equipped with holes or openings to allow the interior to communicate with the exterior.

Commercially available plastic optical fibers, were spliced to the tubes. The optical fibers enable delivery of injected light and remote detection of the output light signal. Plastic fibers used in the experiment were SK-20 and SK-40 types from Mitsubishi Rayon America, Inc. with outside diameters of 500 and 1000 microns. Typically, approximately 1 meter of fiber was cut and polished for splicing to the tubes containing the beads.

With insertion of the optical fibers into the tube during the splicing process, an approximately 2 to 10 mm of tube is occupied with packed beads.

EXAMPLE 6

Example 6 is directed to instrumentation for directing the light signal into and receiving a light signal from the assembly holding the beads enclosed. The instrument features optical sources such as light emitting diodes. In a typical application, a green light emitting diode serves as an active interrogation wave length and a red light emitting diode provides an optical reference. The light emitting diode driver circuitry regulates the output intensity and modulation circuitry independently modulates the light emitting diode signal. Detector circuitry demodulates the signal and provides a lock in amplifier function. The signal undergoes an analog to distal conversion for signal processing and display as required. Signal conditioning for on-line calibration is done in the software.

Figure 4:
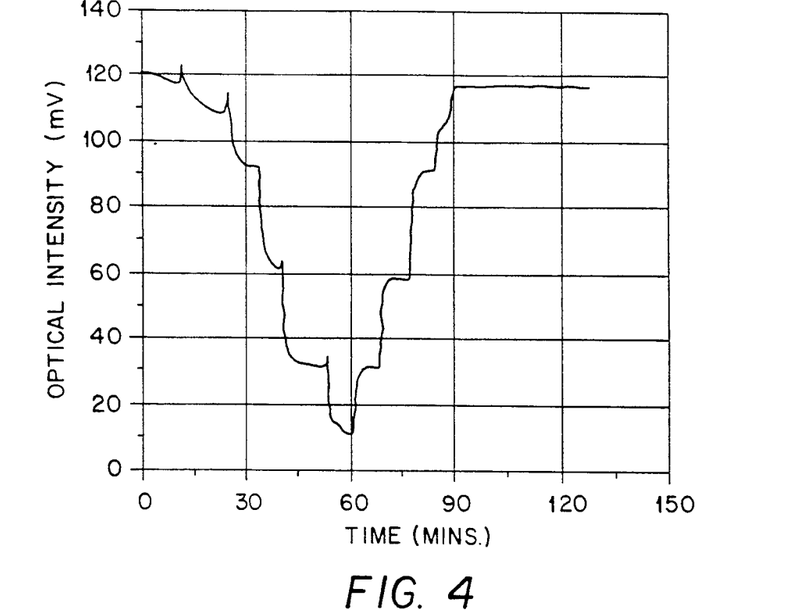
FIG. 4 illustrates graphically a device embodying features of the present invention responding to step changes in pH.
Figure 5:
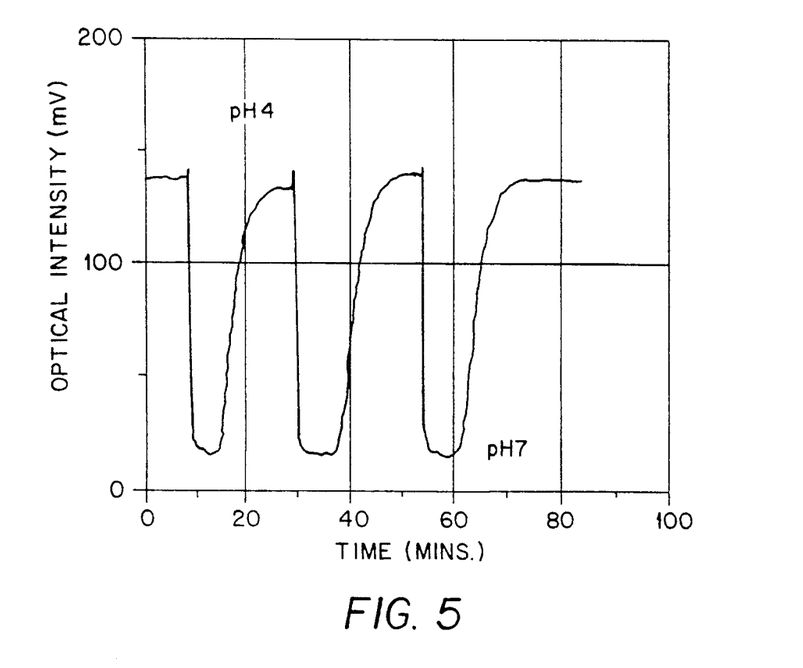
FIG. 5 illustrates graphically a device embodying features of the present invention time responding to changes in pH.

FIG. 4 shows the response of beads enclosed in a polymer substrate made in accordance with Example 1 for measuring hydrogen ion concentration. The Figure depicts a test solution as the pH is stepped between 4.5 and 7. FIG. 5 depicts the response of beads for measuring hydrogen ion concentration as a test solution is cycled between a pH of 4.5 and 7. The data indicates that the sensor is fully reversible and peak to-peak reproducibility is greater than 90%.

Figure 6A:
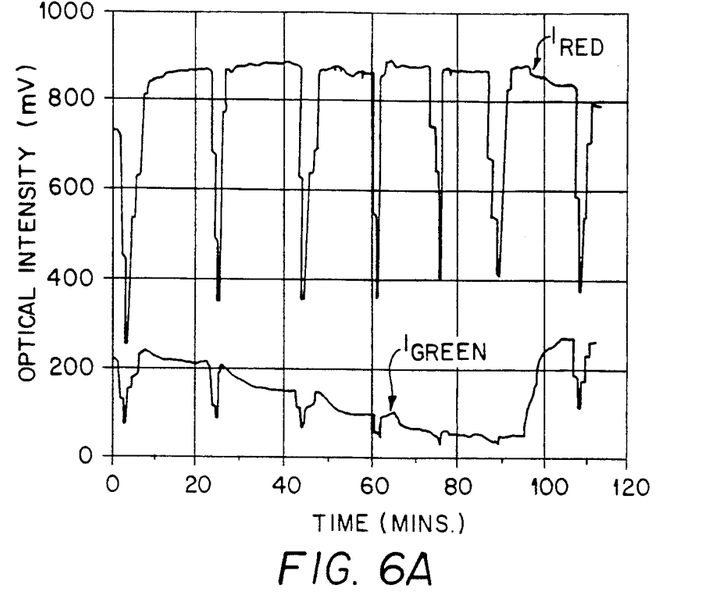
FIG. 6A illustrates graphically a device and supporting instrument embodying features of the present invention responding to step changes in pH in both the green active signal and the red control signal; and, FIG. 6B illustrates graphically the information of FIG. 6A as a ratio of optical intensity.
Figure 6B:
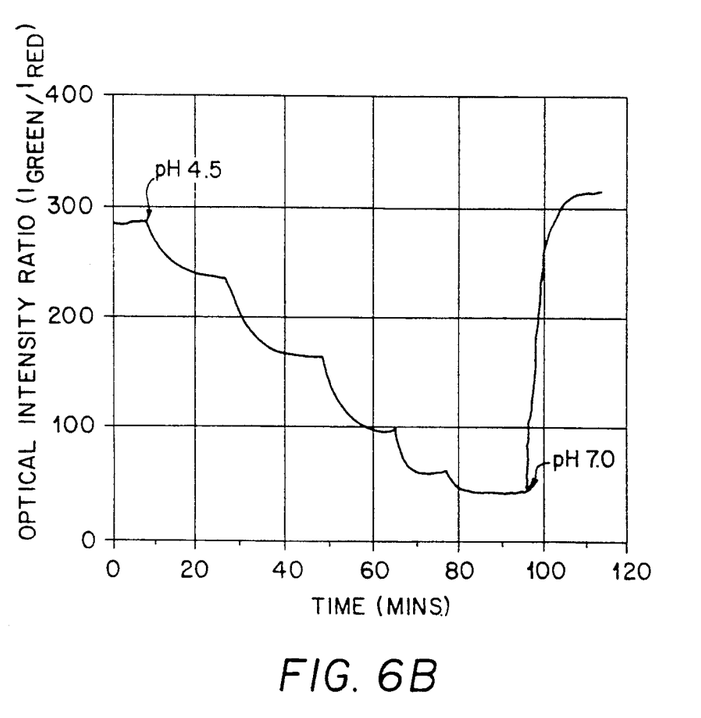

FIGS. 6A and 6B describes transmitted signals at red and green wave lengths as an pH indicator is exposed to stepped changes in pH.

While preferred embodiments of the invention have been described it will be appreciated that variations of the invention may be perceived by those skilled in the art, which variations are nevertheless within the scope of the invention as defined by the claims appended hereto.

What is claimed is:

1. A device for detecting the presence or concentration of an analyte comprising: a sensing element comprising at least one bead having an outer film layer of a polymer substrate, said polymer substrate being capable of receiving and discharging light, and said polymer substrate having a porous matrix and sensing reagent; said sensing reagent being entrapped within and chemically bound to the polymer substrate and having a first absorption spectra in the presence of analyte and a second absorption spectra in the absence of analyte; said porous matrix expanding the effective surface area of said polymer substrate for receiving analyte, said polymer substrate allowing said sensing reagent to alter the spectra of light passing through said polymer substrate in the presence of analyte; and said bead comprising a material for providing mechanical strength to the polymer substrate.

2. The device of claim 1 further comprising light inputting and discharging means in communication with said polymer substrate, said light inputting and discharging means being capable of directing light from a light source into said polymer substrate and receiving light from said polymer substrate.

3. The device of claim 2 wherein said light receiving and discharging means comprise a housing which housing retains said polymer substrate in communication with one or more optical fibers.

4. The device of claim 3 wherein said housing has wall means and two ends defining an interior chamber and an exterior surface, one of said ends having an optical fiber for directing light into said interior chamber, and one of said ends having an optical fiber for receiving light rom said interior chamber, said interior chamber being in communication with said exterior surface by one or more openings in said wall means, and said sensing element being substantially enclosed within said interior chamber.

5. The device of claim 1 wherein said bead is made of glass.

6. The device of claim 1 wherein said sensing element includes a plurality of said beads.

7. The device of claim 6 wherein said bead is approximately 100 to 1000 microns in diameter.

8. The device of claim 6 wherein said polymer substrate film has a thickness of up to about 200 microns.

9. The device of claim 8 wherein said polymer substrate has a pore size of about 50 angstrom to 200 angstroms.

10. The device of claim 1 wherein said sensing reagent has a first absorption spectra and a second absorption spectra in the presence or absence of one or more of the analytes selected from the group consisting of hydrogen ion, hydrazine, ethylene, ammonia, carbon monoxide and water.

11. The device of claim 1 wherein said sensing reagent is selected from the groups of sensing reagents consisting of bromophenol red, bromocresol purple, vanillin, cobalt chloride and palladious chloride.

12. The device of claim 1 wherein said sensing reagent is substantially dispersed in said polymer substrate.

13. The device of claim 1 wherein said polymer substrate is hydrophilic.

14. The device of claim 13 wherein said polymer substrate is 2-hydroxyethyl methacrylate and polyacrylamide.

15. The device of claim 1 wherein said polymer substrate is hydrophobic.

16. The device of claim 15 wherein said polymer substrate is methyl methacrylate and triethylene glycol dimethacrylate.

17. The device of claim 1 wherein said polymer substrate is expanded by the presence of a solvent during a polymerization reaction, which solvent is removed after the polymerization reaction is completed.

18. The device of claim 17 wherein said solvent is an organic solvent.

19. The device of claim 17 wherein said solvent is an inorganic solvent.

20. A method of detecting the presence or concentration of an analyte comprising the following steps:
a) contacting a sample potentially containing analyte with a sensing element comprising at least one bead having an outer film layer of a polymer substrate, said polymer substrate being capable of receiving and discharging light, and said polymer substrate having a porous matrix and sensing reagent; said sensing reagent being chemically bound to the polymer substrate and having a first absorption spectra in the presence of analyte and a second absorption spectra in the absence of analyte; said porous matrix expanding the effective surface area of said polymer substrate, said sensing reagent altering the spectra of light passing through said polymeric substrate in the presence of analyte; and said bead comprising a material which is capable of providing mechanical strength to the polymer substrate; and
b) inputting light into said polymer substrate, said light having a spectra capable of being altered by said sensing reagent; and
c) monitoring light leaving said polymer substrate for alteration indicative of the presence or absence or concentration of analyte.

21. The method of claim 20 wherein said support means and polymer substrate are held in light inputting and discharging means in communication with said polymer substrate, said light inputting and discharging means being capable of directing light from a light source into said polymer substrate and receiving light leaving said polymer substrate.

22. The method of claim 21 wherein said light receiving and discharging means comprise a housing which housing retains said polymer substrate in communication with said one or more optical fibers.

23. The method of claim 22 wherein said housing has wall means and two ends defining an interior chamber and an exterior surface, one of said ends having an optical fiber for directing light into said interior chamber, and one of said ends having an optical fiber for receiving light from said interior chamber, said interior chamber in communication with said exterior surface by at least one opening in said wall means, sensing element being substantially enclosed within said interior chamber.

24. The method of claim 20 wherein said bead is made of glass.

25. The method of claim 20 wherein said sensing element includes a plurality of said beads.

26. The method of claim 25 wherein said bead is approximately 100 to 1000 microns in diameter.

27. The method of claim 25 wherein said polymer substrate film has a thickness of up to about 200 microns.

28. The method of claim 25 wherein said polymer substrate has a pore size of about 50 angstroms to 200 angstroms.

29. The method of claim 20 wherein said sensing reagent has a first absorption spectra and a second absorption spectra in the presence or absence of one or more of the analytes selected from the group consisting of hydrogen ion, ethylene, ammonia, carbon monoxide and water.

30. The method of claim 20 wherein said sensing reagent is selected from the group of sensing reagents consisting of bromophenol red, bromocresol purple, vanillin, cobalt chloride and palladious chloride.

31. The method of claim 20 wherein said polymer substrate is hydrophilic.

32. The method of claim 31 wherein said polymer substrate is 2-hydroxyethyl methacrylate and polyacrylamide.

33. The method of claim 31 wherein said solvent is inorganic.

34. The method of claim 20 wherein said polymer substrate is hydrophobic.

35. The method of claim 34 wherein said polymer substrate is methyl methacrylate and triethylene glycol dimethacrylate.

36. The method of claim 20 wherein said polymer substrate is expanded by the presence of a solvent during a polymeric reaction, which solvent is removed after the polymerization reaction is completed 37. The method of claim 36 wherein said solvent is organic.

38. A method of making a device for detecting the presence or concentration of analyte comprising the following steps:
a) providing a mixture of at least one monomer, sensing reagent and solvent;
b) polymerizing the mixture in the presence of beads to form an outer film layer of a polymer substrate on each of the beads, the polymer substrate including a porous matrix formed by elimination of the solvent and the sensing reagent being chemically bound to the matrix;
wherein said polymer substrate is capable of receiving and discharging light, said sensing reagent having a first absorption spectra in the presence of analyte and a second absorption spectra in the absence of analyte; said porous matrix expanding the effective surface area of said polymer substrate for receiving analyte, said polymer substrate allowing said sensor reagent to alter the spectra of light passing through said polymer substrate in the presence of analyte; and said bead comprising the material for providing mechanical support to the polymer substrate.

39. The method of claim 38 wherein said bead is made of glass.

40. The method of claim 39 wherein said film has a thickness of up to about 200 microns.

41. The method of claim 39 wherein said bead is approximately 100 to 1000 microns in diameter.

42. The method of claim 38 wherein said sensing reagent has a first absorption spectra and a second absorption spectra in the presence or absence of one or more of the analytes selected from the group consisting of hydrogen ion, ethylene, ammonia, carbon monoxide and water.

43. The method of claim 38 wherein said sensing reagent is selected from the group of sensing reagents consisting of bromophenol red, bromocresol purple, vanillin, cobalt chloride and palladious chloride.

44. The method of claim 38 wherein said polymer substrate has a pore size of about 50 angstroms to 200 angstroms.

45. The method of claim 38 wherein said polymer substrate is hydrophilic.

46. The method of claim 45 wherein said polymer substrate is 2 hydroxyethyl methacrylate and polyacrylamide.

47. The method of claim 38 wherein said polymer substrate is hydrophobic.

48. The method of claim 47 wherein said polymer substrate is methyl methacrylate and triethylene glycol dimethacrylate.

49. The method of claim 48 wherein said solvent is organic.

50. The method of claim 48 wherein said solvent is inorganic.

51. The method of claim 38 wherein said polymer substrate is expanded by the presence of a solvent during a polymeric reaction, which solvent is removed by washing after the polymerization reaction is completed.

* * * * *